United States Patent [19]
Rogozinski

[11] Patent Number: 5,395,398
[45] Date of Patent: Mar. 7, 1995

[54] MICROELECTRIC APPARATUS FOR THE ANTISEPSIS, PROMULGATION OF HEALING AND ANALGESIA OF WOUND AND CHRONIC SKIN ULCERS

[75] Inventor: Wallace J. Rogozinski, Azusa, Calif.

[73] Assignee: C. R. Bard, Inc., Murray Hill, N.J.

[21] Appl. No.: 102,986

[22] Filed: Jul. 28, 1993

[51] Int. Cl.6 .......................... A61N 1/04; A61N 1/30
[52] U.S. Cl. ................................ 607/50; 607/46;
                                  607/72; 607/152; 607/153
[58] Field of Search ........................ 607/1-3,
        607/46, 50, 72, 75, 152-153; 604/210; 602/2

[56] References Cited

U.S. PATENT DOCUMENTS

| | | | |
|---|---|---|---|
| 2,493,155 | 1/1950 | McMillan | 607/153 |
| 4,292,968 | 10/1981 | Ellis | 607/75 |
| 4,570,637 | 2/1986 | Gomes et al. | 607/153 |
| 4,619,252 | 10/1986 | Ibbott | 607/2 |
| 4,895,153 | 1/1990 | Pakedchi et al. | 607/50 |
| 4,989,607 | 2/1991 | Keosch et al. | 607/50 |
| 5,085,217 | 2/1992 | Shimizo | 607/152 |
| 5,218,973 | 6/1993 | Weaver et al. | 607/152 |

FOREIGN PATENT DOCUMENTS

| | | | |
|---|---|---|---|
| 0367320 | 5/1990 | European Pat. Off. | 602/2 |
| 8100964 | 4/1981 | WIPO | 607/153 |
| 9111216 | 8/1991 | WIPO | 607/153 |

Primary Examiner—William E. Kamm
Attorney, Agent, or Firm—Dennison, Meserole, Pollack & Scheiner

[57] ABSTRACT

A small, handheld, microelectric, direct current generator with a low frequency modality is applied directly to a wound site through a composite wound covering or dressing. An electric potential difference is established between an anode and cathode of the composite wound dressing. Wound healing is facilitated by the biostimulatory effect of the applied microelectric current on adenosine triphosphate production (ATP), cell membrane transport of amino acids and protein synthesis. The microelectric currents applied through the composite wound dressing, promulgate antisepsis, interfere with the neurological transmission of pain signals and concomitantly stimulate the release of endorphins which helps to relieve the pain associated with wounds, ulcers and other tissue injuries.

13 Claims, 4 Drawing Sheets

MICROELECTRIC APPARATUS FOR THE ANTISEPSIS, PROMULGATION OF HEALING AND ANALGESIA OF WOUND AND CHRONIC SKIN ULCERS

BACKGROUND OF THE INVENTION

1. Field of the Invention

This invention is directed to a method and apparatus for healing wounds. More specifically, to a method and apparatus for healing wounds by an application of low frequency microelectric current.

Chronic wounds and skin ulcers are, typically, contaminated with a variety of microorganisms, both pathogenic and non-pathogenic types. The non-pathogenic types of microorganisms constitute the normal flora of intact skin and may become pathogenic when their numbers overwhelm the natural host defenses in the wound environment and subsequently cause infection. Becker, G. D.: "Identification and Management of the Patient at High Risk for Wound Infection". Head Neck Surg Jan/Feb: 205-210, 1986.

Quantitatively, it has been shown by Kucan, J. O. et al in "Comparisons of Silver Sulfadiazine and Physiologic Saline in the Treatment of Chronic Pressure Ulcers", Amer Ger Soc 29:232-235, 1981, that open wounds can maintain a bioburden of approximately $10^5$ microorganisms per gram of tissue without clinical manifestation of infection. However, a bioburden of greater than $10^5$ is a significant challenge for the local wound tissue defenses. Consequently, a bioburden of $10^6$ microorganisms per gram will often result in wound infection. Robson, M. C. et al., "Bacterial Quantification of Open Wounds", Military Medicine 134:19-24, 1969.

Wounds that are heavily contaminated by microorganisms, but not clinically infected, are often characterized by a prolonged period of inflammation as well as a delay in wound repair and healing. Micro-organisms that contaminate wounds have been implicated as an important factor in the retardation of wound healing by interfering with leukocyte phagocytosis and also by the depletion of nutrients and oxygen required for normal tissue granulation. Ree, B. R. et al., "Cutaneous Tissue Repair: Practical Implication of Current Knowledge, Part II", Journal of the American Academy of Dermatology 13(6): 919-941, 1985.

Historically, wounds have been cleansed and disinfected with a host of different types of antiseptic agents ranging from acetic acid to halogen-based solutions such as complexed iodine. While topical antiseptic agents have the recognized ability to either inhibit or destroy infection producing microorganisms, they also induce chemical trauma and necrosis of the host defense cells, such as macrophages, when used directly in the wound site. Branemark, P. I. et al., "Tissue Injury Caused by Wound Disinfectants", Bone Joint Surg Am 49:48-6.2, 1967 and Lineweaver, W. et al., "Topical Antimicrobial Toxicity", Arch Surg 120:267-270, 1985.

Furthermore, topical antiseptic agents, which are known to be severe cytotoxins, impinge dramatically upon the wound-healing processes and greatly impair the host defense mechanism. Viljanto, "Disinfection of Surgical Wounds Without Inhibition of Normal Wound Healing", Arch Surg 115:253-256, 1980.

Alternatively, minute concentrations of silver ions in solution or in the wound environment demonstrate a pronounced micro-biocidal effect without the corresponding cytotoxic properties generally associated with antiseptic and other non-biocompatible agents used to facilitate wound antisepsis.

Wound healing is also influenced by other factors and interventional methods including the application of low amperage microcurrents. Clinical investigators have established that electro-stimulation can affect every phase of wound healing. Becker, R. "The Direct Current Control System: A Link Between Environment and Organism", N.Y. State, Med 62-1169-1176, 1962; Becker, R., "Electrical Control of Growth Processes", Med Times 95:657-669, 1967a,; and Becker, R. et al., "Method for Producing Cellular Differentiation by Means of Very Small Electrical Currents", Trans N.Y. Acad Sci 29:606-515, 1967b.

Direct galvanic or low intensity direct current delivered to the wound site, in a steady state or as pulsed electrical stimulation, at current intensities between 0 to 1000 microamperes increased adenosine triphosphate (ATP) levels and improved protein synthesis. Wolcott, L. et al., "Accelerated Healing of Skin Ulcers by Electrotherapy: Preliminary Clinical Result", South Med 62:795-801, 1969.

The process by which ATP synthesis occurs has been postulated by numerous investigators: Davis, R. V., "Therapeutic Modalities for the Clinical Health Sciences", 1st ed., 1983, Copyright, Library of Congress TXU-389-661; Griffin, J. E. et al., "Physical Agents for Physical Therapists", 2nd ed., Springfield, Charles C. Thomas, 1982; Krusen et al., "Handbook of Physical Medicine & Rehabilitation", 2nd ed., Philadelphia, W. B. Saunders Company, 1971: and Schriber W. A., "A Manual of Electrotherapy", 4th ed., Philadelphia, Lea & Feiblger, 1975.

In this process, electrons stimulated by microcurrents react with water molecules at the anode to produce positively charged hydrogen ions and in similar fashion, negatively charged hydroxyl ions are formed at the cathode. An electrical potential with a corresponding proton gradient is created between the anodic and cathodic poles, as well as between the cell wall of the tissue and intracellular fluid. When moving electrically charged hydrogen ions transverse the tissue cell wall and encounter the membrane of the mitochondria, (an intracellular organelle), with its stores of Adenosine triphosphatase, (the enzymatic catalyst of ATP production), the Adenosine triphosphatase is activated to enhance the manufacture of ATP. ATP is utilized as the energy resource for the endothermic synthesis of important proteins.

Amino acids, the building blocks of proteins, are transported by the electrical gradients through the mitochondrial membrane and synthesized into proteins by means of energy made available by ATP.

Physiological evidence of the biostimulatory effects of microcurrent application to wounds was reported by Alaverez, Om., et al., 1983, J. Invest. Dermatology, 81(2), 144, where they observed "a marked increase in the synthesis of collagen and the rate of epithelial regeneration, which are key aspects of wound healing".

In a carefully controlled in-vitro study, Nessler, J. P., Mass. O.P. Clinical Orth, Rel, Res., (217), 303 demonstrated that "transected rabbit tendons grown in culture medium responded to microcurrent stimulation of 7 uA with a 91% higher uptake of proline and 255% greater hydroxyproline activity, both of which are important biochemical constituents of tissue repair, than the unstimulated control".

Numerous other investigators have found that low intensity direct current enhanced the wound healing process. Carley, P. J. et al., 1985, Arch Phys Med Rehab, 66, (7), 443-446, described a "150-250% improvement in the rate of healing decubitus". Gault, W. et al., 1976, Physical Therapy, 56 (3) 265, "treated 106 ischemic skin ulcers with microcurrents which ranged from 200-800 uA and found that the ulcers treated healed twice as fast as those that were untreated". Wolcott, L. D. et al., 1969, South Med J., 62,796-801 "treated a group of 67 patients with low intensity direct electrical currents and reported an increased in the rate of healing over the control group."

Electro-analgesis has been known for a number of years. Medical devices which are designed for the application of small electrical currents to the human body subscribe to the theory of Transcutaneous Electrical Nerve Stimulation (TENS) or Electro Galvanic Stimulation (EGS) to afford pain relief without the use of analgesic drugs which have a potential for patient misuse and habituation. In theory and practice, electrocurrents in micro- or milli-ampere range are applied to the body, through a pair of oppositely charged skin electrodes, which block the neuro-transmission of pain signals and/or reduce the perception of pain by directly influencing the release of endorphins, a natural analgesic produced endogenously. Goldstein, A., "Opid Peptides (Endorphins) in Pituitary and Brain", Science, 1976:193:1081-1086 and Guillenum, R., "Endorphins, Brain Peptides that Act like Opiates", N. Eng J Med 1977, 4:226-228.

Holloway, A. G., "Lower Leg Ulcers: An Overview", Chronic Wound Care: Health Management Publications, Inc., 1990, specifically states that "Characteristic symptoms of wounds classified as arterial ulcers generally involve pain."

Partial thickness wounds accompanied by inflammation and edema are uniformly painful. Experimentally, it has been proven that microampere electrical stimulation does mitigate pain secondary to tissue injury inasmuch as it has been shown that naloxone hydrochloride will block the palliative effects of the low level electrical stimulation by interfering with the opiate receptor sites in the brain. Sjolund, B. et al., "Electro Acupuncture and Endogenous Morphines", Lancet 1976:2:1085 and Hosobachi, Y. et al., "Pain Relief By Electrical Stimulation of the Central Gray Matter in Humans and Its Reversal by Naloxone", Science 1977:197:183-186.

SUMMARY OF THE INVENTION

A small, handheld, microelectric, direct current generator produces a current having an amplitude of about 0 to 1000 microamperes with a frequency range of about 0.3 to 292 pulses per second. The generator is selectively connected to a device or apparatus which operates as a wound dressing or covering. The device comprises an electro-conductive hydrogel such as a hydrophilic, adhesive polymer which is adhered to a flexible plastic or non-woven support layer. A first electrode, consisting of a pure silver anode, passes through the support layer and the hydrogel. A second electrode, consisting of a base metal cathode, surrounds the anode and is mounted on the support layer which is an electro-conductive, hydrophilic, adhesive polymer. The cathode does not pass completely through the hydrogel. The hydrogel is formed in two concentric rings, one of which surrounds the anode and the other one of which engages the cathode.

The generator establishes an electric potential differential between the anode and cathode of the composite wound dressing apparatus. Consequently, the microelectrical stimulation of the anode readily ionizes the pure silver into positively charged particles which are driven, by the microcurrent, in the direction of the cathode. The charged silver ions exert a lethal effect upon bacteria and other microorganisms that contaminate the wound environment through a process called oligodynamic action.

Wound healing is facilitated by the biostimulatory effect of the applied microelectric current on adenosine triphosphate (ATP) production, cell membrane transport of amino acids and protein synthesis.

Microelectric currents applied through the composite wound dressing also interfere with the neurological transmission of pain signals and concomitantly stimulate the release of endorphins, the body's naturally occurring analgesic, which helps to relieve the pain associated with wounds, ulcers and other tissue injuries.

DESCRIPTION OF THE INVENTION

Figures 1, 2, 3:
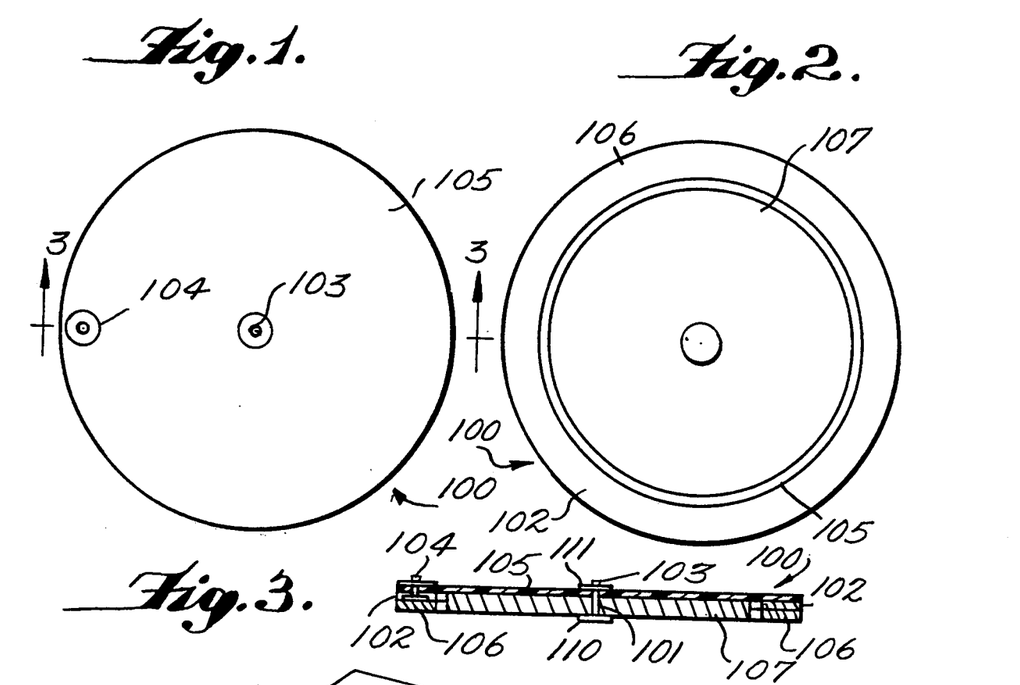
FIG. 1 is a top plan view of the apparatus of the instant invention.
FIG. 2 is a bottom plan view of the apparatus of FIG. 1.
FIG. 3 is a cross-Sectional view of the apparatus shown in FIG. 1.

Referring now to FIGS. 1, 2 and 3 concurrently, there is shown a preferred embodiment of the applicator apparatus of the instant invention.

The applicator apparatus consists of a bipolar, electro-stimulating pad (ESP) 100 configured as a circle or an ellipse. The ESP 100 includes a dorsal support surface layer 105 which is composed of an adhesive-coated, electrically inert, flexible plastic or non-woven cloth material. The support layer 105 is laminated to contact surface layers 106 and 107. The layers 106 and 107 are constituted of an electrically-conductive hydrogel polymer such As commonly used in the art. The polymer layers embody the surfaces that abut the integument and/or wound opening when in use. The hydrogel polymer exhibits both electro-conductive and adhesive properties. Thus, when applied to a wound site, the hydrogel polymer adheres firmly to the intact skin surrounding the wound.

As seen in the Figures, the layers 106 and 107 are arranged in concentric rings with layer 106 encircling layer 107.

In an alternative configuration, the flexible plastic or non-woven backing (FIG. 1) may be radially extended beyond the circumference described by the hydrogel polymer to thereby provide an additional adhesive surface to secure the ESP 100 to the wound margin.

The anode 101 is a single pole located at the center of the ESP 100. The anode 101 is fabricated of pure silver. In a preferred embodiment, the anode 101 includes a flat surface 110 at the inward end thereof. An attaching clip, stud or terminal 103 is provided at the outward end of anode 101. An outer securement surface 111 is provided at the outward end of anode 101. The cathode 102 consists of an electrically conductive ring disposed at the circumference of the ESP 100. The peripheral ring of the cathode 102 substantially surrounds the anode 101. The anode 101 and cathode 102 are connected to separate electro-conductive terminal 103 and terminal Or stud 104 through the composite materials of the ESP 100 and attached at the dorsal surface 105 of the ESP 100. These terminals 103, 104 are provided as the coupling points for a direct current microampere electrical generator discussed infra.

The attaching stud 103 for the silver anode 101 and the attaching stud 104 for the metallic cathode 102 are punched through the composite materials of the ESP 100 and secured in position by swaging them together with electrical terminal snap connectors. The cathode stud 104 is joined to the cathode ring 102 and substantially embedded in the outer ring 106 of polymer. The anode stud 103 passes completely through the inner ring 107 of the polymer. The inward surface 110 of the anode stud 103 is arranged to make contact with the surface of the patient.

Figure 4:
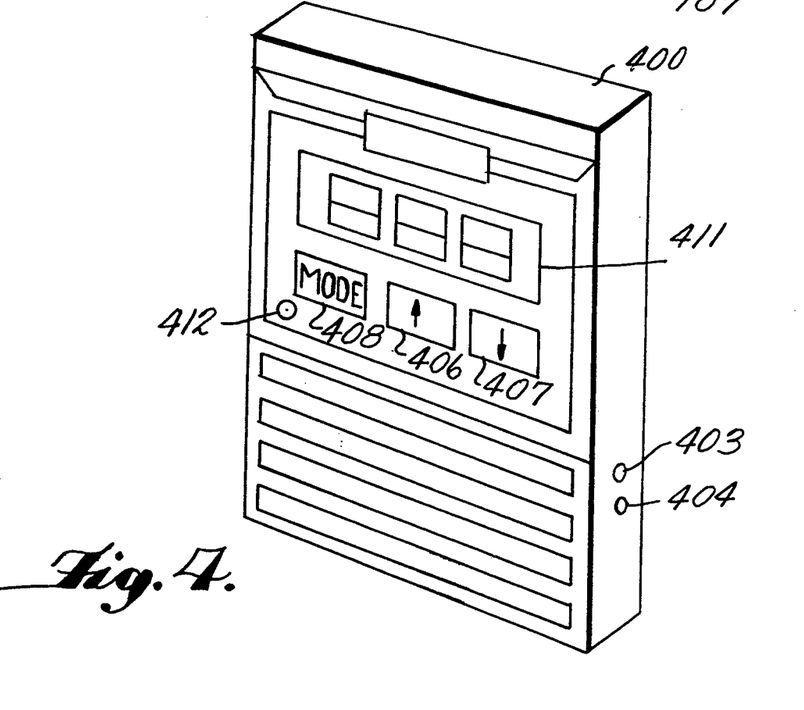
FIG. 4 is an embodiment of a control device which incorporates a circuit of the instant invention when attached to the apparatus shown in FIGS. 1-3.
Figure 5:
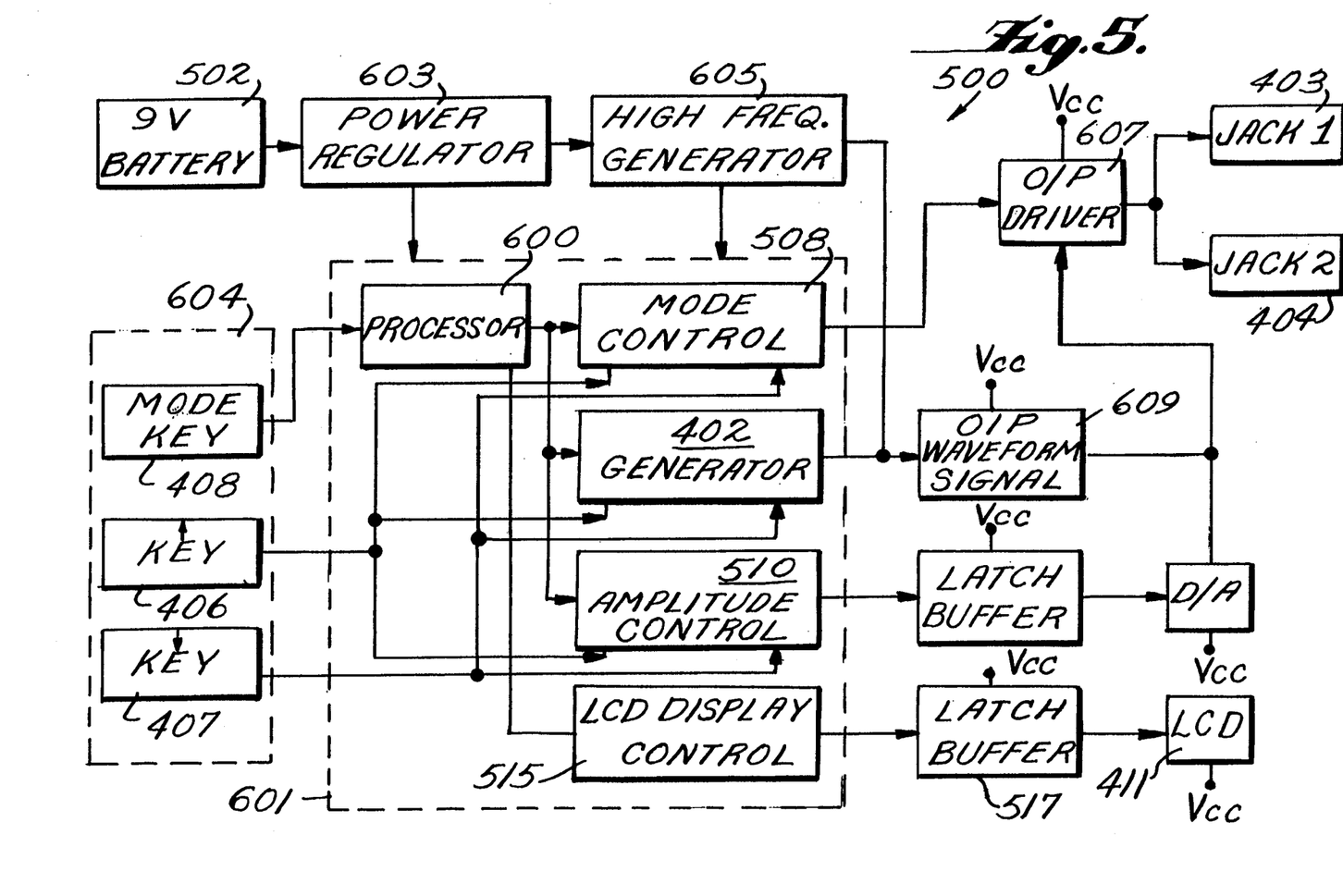
FIG. 5 is a block diagram of an electrical circuit for producing a low frequency, microelectric current to be applied to the apparatus shown in FIGS. 1-3.

Referring now to FIGS. 4 and 5, there is shown a representative small, handheld, microampere direct current unit 400 with a selectable range of microcurrent output (for example, 0 to 1000 uA). The handheld unit 400 includes a generator 402 capable of operation in either steady state or pulsed frequency (for example, 0.3 to 292 pulses per second). The unit additionally includes a high frequency generator or oscillator 605 for this specific purpose. Both generators 402 and 405 are attached to the electrical terminal snap connectors 103 and 104, shown in FIG. 1, utilizing, for example, low resistance, shielded wires (not shown) fitted with appropriate pin and snap connectors at the ends thereof. Easy attachment is facilitated by inserting the pins into jacks 403 and 404 provided in the unit 400. The snap connectors of the wires are attached to the ESP 100 by way of the snap connectors 103 and 104.

By operation of the touch contact switches or control keys 406, 407, the output frequency of the signal at jacks 403 and 404 can be controlled. Also, mode key 408 provides manual mode selection capabilities. The output frequency of the output signal is displayed at the display 411. Additionally, light indicator 412 provides a visual power on/off indication.

Referring concurrently to FIG. 5, there is shown a block diagram of circuit 500 of handheld unit 400. The microampere circuit 500 is electrically driven by one 9 volt alkaline battery 502. The microcurrent circuit 500 has the capability to be used as a DC dual channel steady state continuous or pulsed current stimulation device with current ranges from 1 uA to 1000 uA. The device is controlled by a microprocessor 601 that is, also, capable of being used both as a preset specific frequency device or as a variable frequency device by the use of the mode selector switch or key 408. Additionally, a mode control 508 provides the device the capabilities of varying the frequencies from 0.3 to 292 Hz. The mode key switch 408 selects and adjusts current frequency and amplitude together with arrow keys 406 and 407. This allows a manual selection for the user.

An electronic digital readout or LCD display control 515 monitors and displays the microampere output and frequency when in use. In the embodiment shown, the display 411 can be a liquid crystal display (LCD) which includes a latch buffer 517. The circuit 500 of the microcurrent generator 400 is housed and electrically isolated in the small handheld unit shown in FIG. 4.

Figure 6:
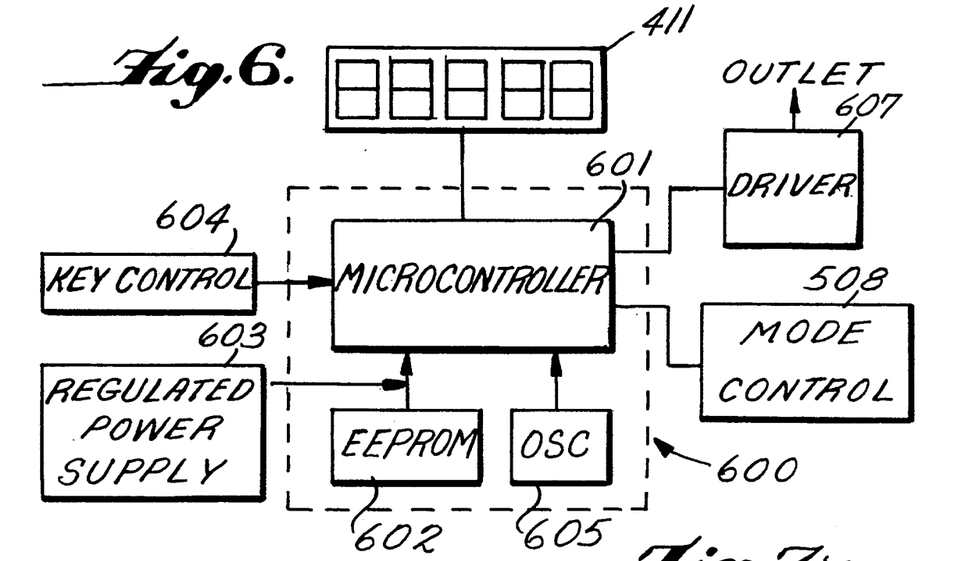
FIG. 6 is a block diagram of a processor control circuit of the present invention.

Referring now to FIGS. 5 and 6, there is shown a block diagram of a processor control circuit 600 of the micro-processor 510.

The circuit 600 includes a micro-controller 601 of any conventional configuration. Typically, a preprogrammed 87C51 micro-controller is utilized. This unit receives and processes instructions from 604 (mode key, ↑ key, ↓ key) and processes the instructions as "mode control" (+, −, +/−), frequency generator, channel 1 amplitude, channel 2 amplitude and controls the LCD.

A regulated power supply 603 is connected to the micro-controller 601. The power supply 603 also provides power to other portions of the circuit 600 as is appropriate. The regulated power supply 603 provides a regulated supply signal to the circuit 600.

An EEPROM 602 is connected to micro-controller 601. The EEPROM 602 is an electrically erasable, programmable, read-only memory which provides signals to the micro-controller 601. The EEPROM 602 is-also used as a memory for the micro-controller 601. The EEPROM stores signals therein which are representative of the operation of the circuit. The last control settings utilized for frequency and wave form are stored and referenced until new parameters are manually entered through control keys 510, 512 and 514.

An oscillator 605 is connected to the micro-controller 601 to provide a suitable frequency signal thereto. The oscillator 605 is any suitable Oscillator such as a crystal-controlled oscillator or the like which can provide a high frequency signal to the micro-controller 601. Depending upon the operation of the micro-controller 601, the frequency signal from oscillator 605 can be divided or otherwise reduced to produce any number of desirable frequency signals.

A key control circuit 604 is connected to provide control signals to the micro-controller 601 in order to select the frequency of the signals supplied thereby. The key control device 604 is connected to the micro-controller 601 to determine the mode of operation of the micro-controller and, through switches or the like, is then able to increase or decrease the output signal produced by the micro-controller 601.

The liquid crystal display device 411 is connected to the micro-controller 601. The LCD device 411 displays the frequency of the signal which is being generated by micro-controller 601 as a result of the operation of the oscillator 605 and the key control 604.

The mode control 508 is connected to an output of micro-controller 601 to select the mode of operation of the output signal. The mode control 508 receives the signal from the micro-controller 601 to determine what mode of operation is to be provided.

A O/P driver 607 is connected to an output of the micro-controller 601 and an output of the mode controller 508. The driver 607 is connected to supply output signals to the ESP device 100 noted above in accordance with the signal supplied thereto.

The driver 607 then supplies signals to the ESP device 100 described above in response to signals supplied to driver 607 by micro-controller 601.

Figure 7A:
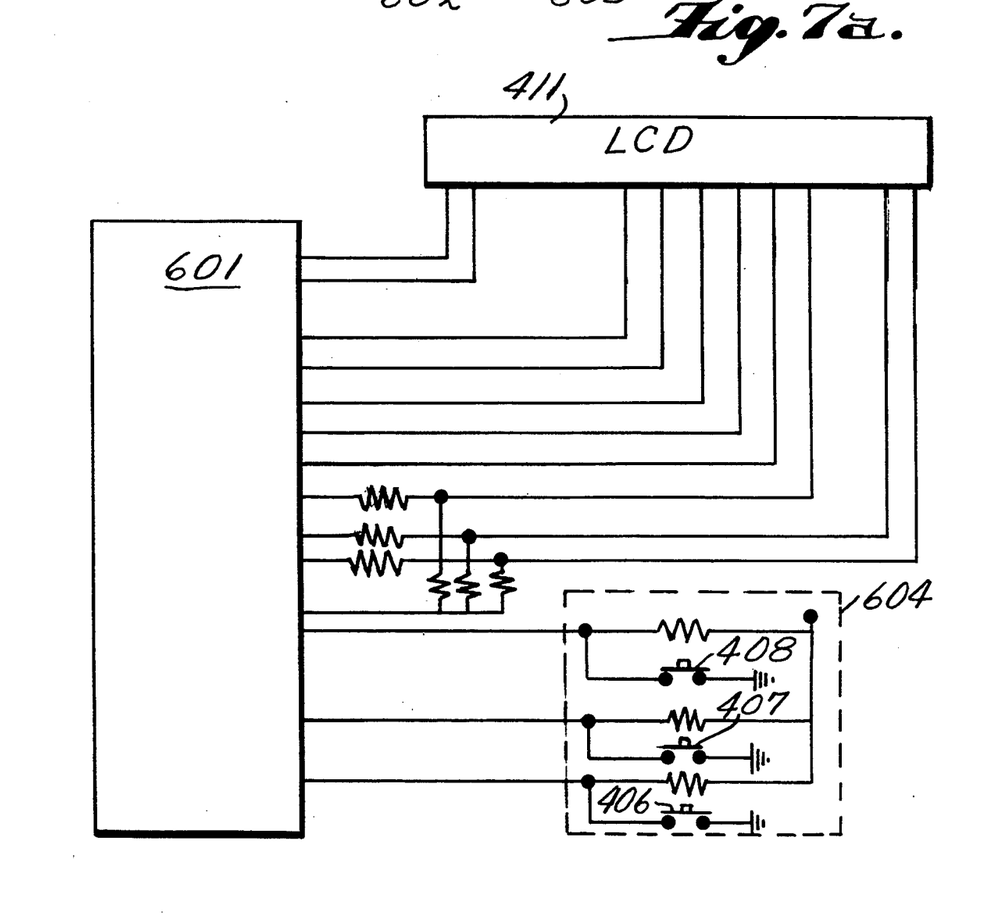
FIG. 7A is a schematic diagram of a LCD readout circuit of the present invention.

Referring now to FIG. 7A, there is shown in greater detail a portion of the circuit shown in FIG. 6. In particular, the micro-controller 601 is connected to the LCD display 411 by means of a plurality of lead lines. In particular, there are shown a number of voltage dividers which are connected to supply specific voltages to certain terminals of the LCD. The other terminals are connected to individual terminals or ports of the micro-controller 601 in order to provide specific signals to specific symbols, characters or portions thereof in the display 411.

The display 411 is conventional in design and provides the output display indicator 412 which is representative of the signal being provided to the output network connected to the ESP device 100. Thus, the LCD 411 includes, in the embodiment illustrated, a seven-segment display for each character and is operated in a conventional manner in response to the signals from the micro-controller.

The key controller 604 comprises a plurality of switches or keys 408, 407 and 406 which are connected between ground and, effectively, the control voltage provided by the regulated power supply 603. The switches can be any type of switch including pressure switches, push buttons or the like mounted on the front face of handheld unit 400. Thus, mode switch 408, when operated, selects the mode of operation of the device. For example, mode key 604 can select any of the following when pushed: Mode control 508 selects polarity, positive (+), negative (−), bi-polar (+/−); frequency control 402 selects range from 0.3–300 HZ; or amplitude control 510 selects range from 0–100 microampere with a resolution of 5 microampere.

For example, whenever the decrementing switch 407 is operated, the signal supplied by the micro-controller 601 is decremented by a factor of 1 Hz. (i.e. cycles per second). Conversely, when the incrementing switch 406 is activated, the frequency of the signal supplied by micro-controller 601 is increased by 1 Hz.

The regulated power supply 603 comprises the battery 502 which is connected to a voltage controller device which regulates the battery voltage within + or −0.5 volts. Thus, when the battery voltage output deteriorates to a level of approximately 5.5 volts, the regulator device is turned off so that no voltage is supplied at the output terminal VCC. Thus, the system is shut down to avoid inaccurate operation due to a low voltage problem.

Figure 7B:
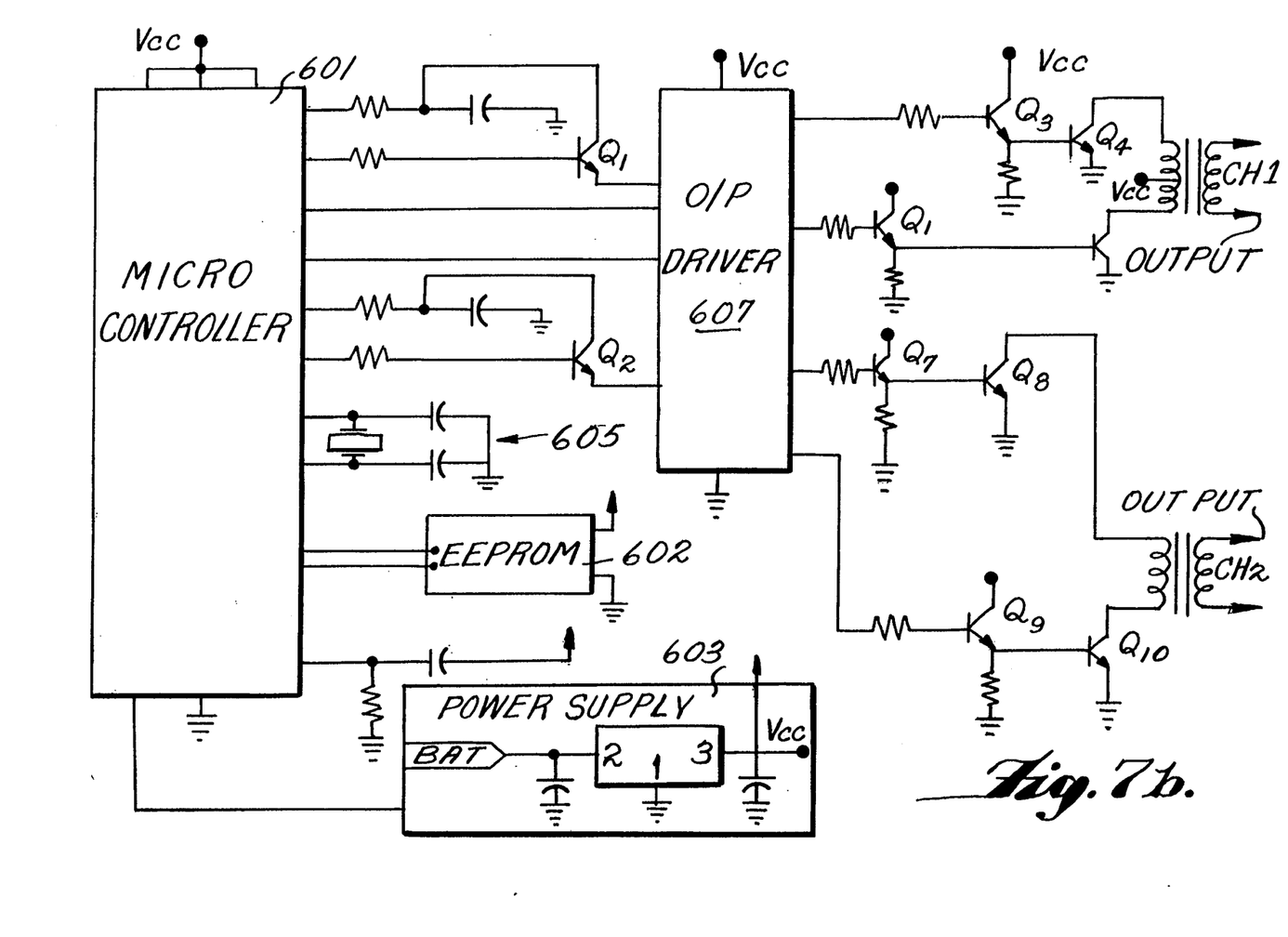
FIG. 7B is a schematic diagram of the present invention.

As shown in FIG. 7B, shunt capacitors are provided at the input and output terminals of the voltage regulator device 603 so that spikes or noise signals are not supplied to the circuit 600.

As noted, the regulated power supply 603 is connected to the micro-controller 601 by means of an additional filter network comprising a coupling Capacitor and an impedance path to ground which prevents inappropriate signals from being supplied to the micro-controller.

The EEPROM 602 is connected to appropriate terminals at the micro-controller. The EEPROM 602 also receives the control voltage VCC. Consequently, the regulated power supply 603 is desirable to prevent spurious signals from being supplied to the EEPROM 602.

The EEPROM 602 is operated to include signals representative of current, frequency and waveform. EEPROM 602 saves in short term memory the frequency and waveform (+, −, +/−) settings which may be read by the micro-controller 601. The amplitude is not stored and must be set. Thus, the signals are supplied to the micro-controller 601 and vice versa in order to control the operation of the circuit.

The oscillator 605 is also connected to supply high frequency signals on the order to 6 MHz. to the micro-controller. These signals are supplied via coupling capacitors. The signals are related to a common ground wherein a bipolar frequency signal is supplied to the micro-controller.

Also referring to FIG. 7B, there is shown a quad bilateral switch circuit or O/P driver 607 which is, typically, a model 4066 manufactured by any of the current manufacturers, such as Motorola, NEC or others.

The circuit 607 is connected directly to the micro-controller 601 to receive signals which represent the output waveform. Likewise, the circuit 607 is connected to the micro-controller circuit via the driver circuit comprising transistors Q1 and Q2, respectively. These transistors are controlled by the signals generated in the micro-controller 601 to effect operation of the 607 circuit.

At each of the outputs of the 607 circuit are provided a pair of Darlington circuits Comprising transistors Q3 through Q10, inclusive. Each Of the Darlington pairs is connected to one terminal of the primary winding of a transformer T1 or T2. The opposite ends of the primary winding is connected to another of the Darlington pairs. The primary winding is center-tap Connected to the bias voltage VCC, wherein the operation of the driver circuit is to provide a push-pull operation in the primary winding of the respective transformer.

The output of the respective transformers are connected to appropriate leads or coupling lines which are then connected to the anode 101 and cathode 102 of the ESP device 100, respectively.

Irrespective of which control circuit is utilized, the ESP can be used topically to Control clinically diagnosed or manifest wound infections, as well as to significantly reduce the large numbers of microorganisms that constitute the biological burden on the living tissue of an open chronic wound. In practice, the ESP 100 is placed directly over the wound cavity or affected area and secured by the adhesive hydrogel polymer rings 106/107. Alternatively, the ESP can be secured to the intact skin surrounding the wound margin by adhesive tape. The microcurrent generator 400 is attached to the ESP via the connecting wires by coupling the positive conducting current wire to the centrally located silver anode snap connector. In similar fashion, contact is established between the negative conducting current wire and the cathode.

The small handheld unit 400 is then activated by the ON/OFF switch and the microcurrent is adjusted between 0–1000 uA by changing the position of the variable current switch. The output current is monitored on the electronic digital display 411. If pulsed direct current is preferred, the variable pulse frequency modulation switch is activated, by way of the mode control 508, and the frequency to be used is selected and monitored through the display 411.

Upon application of a microcurrent to the wound through the ESP 100, the silver of the anode 101 is ionized, commensurate with the intensity of the microampere current. Subsequently, silver ions are driven toward the cathode 102 along the lines of the electrical potential gradient which is equal in all directions from the anode 101 because of the annular configuration of the cathode 102.

Small amounts of the positively charged silver ions (silver ion concentrations estimated to be as low as 0.5 ppm) exert a bactericidal effect upon most microorganisms contaminating the wound bed by means of oligodynamic action, thereby affecting wound antisepsis.

Concurrently, the applied microcurrents stimulate the production of protons at the anode 101, with a corresponding proton gradient that is formed across the tissue cell wall, which also involves the intracellular fluid. Protons which traverse the intracellular fluid and encounter the mitochondrial membrane chemically bind adenosine triphosphate (ATP). The formed ATP then acts as the energy resource for the intracellular synthesis of proteins from the available essential amino acids that have been transported across the mitochondrial membrane. The synthesized proteins constitute the building blocks of living tissue which ultimately are the most important ingredients in the wound healing process.

Pain and local discomfort is commonly associated with most wounds and local tissue trauma. Pulsed microcurrents through the ESP device 100 provides temporary analgesia by interrupting the transmission of pain signals across the neurons and also by stimulating the release of endorphins, the body's own pain killers.

All three actions: antisepsis, wound healing and analgesia, occur simultaneously when microcurrents are applied through the ESP device 100 to a wound or irritated integument.

Some chronic wounds or ulcers develop as a consequence of a primary disease process. For example, those persons afflicted with diabetes typically exhibit very poor peripheral vascular circulation, especially of the lower extremities. Skin breakdown, chronic wounds and ulcers are common among active, insulin-dependent diabetics. Most diabetic foot and leg ulcers are slow to heal and quite prone to serious infections, many of which result in life-threatening gangrene that can only be resolved, in many cases, by surgical amputation of the limb. Administration of microcurrents, through the ESP device 100, to a bacterially contaminated diabetic leg or foot ulcer can provide a high degree of prophylaxis against infection, as well as stimulate the body's tissue to manufacture ATP, an essential requirement of protein synthesis and wound healing.

Venous stasis ulcers are secondary to venous stasis disease which is a consequence of prolonged venous hypertension which is traceable to a condition known as deep vein thrombosis. Chronic pain invariably accompanies venous stasis ulcers and adds to the misery of the patient. Long-standing venous stasis ulcers, including the intermittent cycle of ulcer formation and healing, predisposes the patient to poor capillary perfusion and progressive ulceration. Application of microcurrents in a pulsed direct current mode will afford the patient some palliative control of the pain associated with venous stasis ulcers and also impart some of the other benefits, described earlier, with the use of low intensity currents.

Patients with surgical wounds and incisions historically are treated with strong analgesics and/or opiate drugs to help mitigate the pain and discomfort which is intimately bound to virtually all post-surgical trauma.

The use of the ESP device 100 can help to reduce the requirement for the amount of habit-forming analgesics required to provide relief from pain associated with post-surgical wounds and also to provide a means to reduce the great numbers of infection-causing bacteria.

ESP 100 represents a unique combination of therapy which carefully addresses the major aspects of wound care.

Thus, there is shown and described a unique design and concept of a method and apparatus for healing of wounds using microelectric currents or prescribed frequencies. The particular configuration shown and described herein relates to the application of a microelectric current from a handheld generator to a wound site through a composite wound dressing device. While this description is directed to particular embodiments, it is understood that those skilled in the art may conceive other modifications, variations or changes to the specific embodiments shown and described herein. Any such modifications, variations or changes which fall within the purview of this description are intended to be included therein as well. It is understood that the description herein is intended to be illustrative only and is not intended to be limited only by the claims appended hereto.

I claim:

1. A microelectric apparatus having a generator and a direct current battery, said battery for supplying power to said generator, and said generator generating microelectric current to a site including an open wound or chronic skin ulcers for antisepsis, analgesia and promulgation of healing of said site, said apparatus comprising:

a composite wound dressing for covering said site and electrically connected to said apparatus for applying said microelectric current directly to the wound site through said composite wound dressing, wherein said composite wound dressing including a flexible support layer, and an electro-conductive hydrogel for adhering to said flexible support layer; and a pair of electrodes connected to said generator, said pair of electrodes including a first electrode having a pure silver anode passing through said support layer and the hydrogel to be in direct contact with said site and a second electrode having a base metal cathode for surrounding said anode and mounted on the support layer, said pair of electrodes for establishing an electric potential difference in the composite wound dressing, and stimulating concomitantly a release of endorphins to relieve pain associated with the wound.

2. The small microelectric direct current apparatus of claim 1, wherein said flexible support layer is plastic material.

3. The microelectric direct current apparatus of claim 1, wherein said flexible support layer is a non-woven material.

4. The microelectric direct current apparatus of claim 1, wherein said cathode is mounted on said support layer.

5. The microelectric direct current apparatus of claim 4, wherein said support layer is an electro-conductive, hydrophilic, adhesive polymer.

6. The microelectric direct current apparatus of claim 1, wherein said hydrogel is formed in at least two concentric rings, said first ring surrounding said anode and said second ring engaging said cathode.

7. A microelectric apparatus for applying a low microelectric current to an open wound, said apparatus comprising:
- a composite wound applicator having at least an inner and outer surface layers formed of electrically conductive hydrogel polymer, and a support layer positioned between and contacting said inner and outer surface layers;
- a pair of electrodes including a pure silver anode passing through said support layer and said inner surface layer for direct contact with said open wound, and a base metal cathode surrounding said anode and passing through said support layer to contact said outer surface layer;
- generator means, electrically connected to said pair of electrodes, for supplying the microelectric current to said applicator; and
- control means electrically connected to said generator means for controlling an amount of said microelectric current to said wound.

8. The microelectric apparatus of claim 7, further comprising:
- a battery connected to said control means for electrically driving said apparatus.

9. The microelectric apparatus of claim 8, wherein said generator means includes a high frequency generator.

10. The microelectric apparatus of claim 8, wherein said generator means capable of operating in a steady state mode and a pulsed frequency mode.

11. The microelectric apparatus of claim 8, wherein said control means includes a microprocessor connected to said generator and a memory connected to said microprocessor for storing signals for operating the apparatus.

12. The microelectric apparatus of claim 11, wherein said control means includes a key control circuit connected to said microprocessor for selecting control signals, and a display for displaying the control signals.

13. The microelectric apparatus of claim 11, wherein said microelectronic current is in a range covering 0 to 1000 uA, and a pulsed frequency of 0.3 to 292 pulses per second.

* * * * *

UNITED STATES PATENT AND TRADEMARK OFFICE
CERTIFICATE OF CORRECTION

PATENT NO. : 5,395,398

DATED : March 7, 1995

INVENTOR(S) : Wallace J. Rogozinski

It is certified that error appears in the above-identified patent and that said Letters Patent is hereby corrected as shown below:

Column 10, line 53, "small" should be deleted.

Signed and Sealed this

Twenty-fifth Day of April, 1995

*Attest:*

BRUCE LEHMAN

*Attesting Officer*     *Commissioner of Patents and Trademarks*